US009370240B2

(12) United States Patent
Jimenez et al.

(10) Patent No.: US 9,370,240 B2
(45) Date of Patent: *Jun. 21, 2016

(54) TOOTHBRUSH INCLUDING KIT FOR DECORATING THE TOOTHBRUSH

(71) Applicant: COLGATE-PALMOLIVE COMPANY, New York, NY (US)

(72) Inventors: Eduardo Jimenez, Manalapan, NJ (US); David K. Lee, East Brunswick, NJ (US); Quang Nguyen, Hillsborough, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/642,949

(22) Filed: Mar. 10, 2015

(65) Prior Publication Data
US 2015/0182015 A1    Jul. 2, 2015

Related U.S. Application Data

(63) Continuation of application No. 13/992,167, filed as application No. PCT/US2011/060294 on Nov. 11, 2011, now Pat. No. 9,016,471, which is a continuation-in-part of application No. PCT/US2011/031670, filed on Apr. 8, 2011.

(60) Provisional application No. 61/424,730, filed on Dec. 20, 2010.

(51) Int. Cl.
*A46B 15/00* (2006.01)
*A61C 17/22* (2006.01)

(52) U.S. Cl.
CPC ......... *A46B 15/0091* (2013.01); *A46B 15/0002* (2013.01); *A46B 15/0087* (2013.01); *A46B15/0089* (2013.01); *A46B 15/0097* (2013.01); *A61C 17/22* (2013.01); *A61C 17/225* (2013.01); *A46B 2200/1066* (2013.01)

(58) Field of Classification Search
CPC ............ A46B 15/0002; A46B 15/0087; A46B 15/0089; A46B 15/0091; A46B 15/0097; A46B 2200/1066; A46B 15/0085; A61C 17/22; A61C 17/225
USPC ........... 206/229, 361–362.3, 368–369, 459.5, 206/460, 461–471; 15/105, 143.1, 167.1; 132/308–311
See application file for complete search history.

(56) References Cited

U.S. PATENT DOCUMENTS 1,886,842 A * 11/1932 Shaw ...................... B29C 65/74
                                                                 206/460
3,589,823 A    6/1971 Hendrickson
(Continued)

FOREIGN PATENT DOCUMENTS

EP    0 683 995    11/1995
JP    2001 258646    9/2001
(Continued)

OTHER PUBLICATIONS

Colgate, Kids LEGO Toothbrush, dentist.net; website: http://www.dentist.net/colgate-lego-toothbrush.asp, copyright 1999-2010.
(Continued)

*Primary Examiner* — Bryon Gehman

(57) ABSTRACT

A kit for decorating a toothbrush includes a package, a toothbrush, and at least one of a sticker panel comprising a plurality of stickers and a plurality of decorative bands. The sticker panel may include three panel sections with at least one of the panel sections having stickers thereon. The decorative bands are sized to fit around an outer perimeter of a base portion of the toothbrush for decoration. Thus, the decorative bands are formed of an elastic material to facilitate stretching of the decorative bands to fit around the outer perimeter of the base portion of the toothbrush. The kit may include at least one sticker sized to fit on the base portion of the toothbrush. The kit may also include a panel including one or more stickers and/or one or more decorative bands.

17 Claims, 6 Drawing Sheets

(56) References Cited

U.S. PATENT DOCUMENTS

| | | |
|---|---|---|
| 5,875,796 A | 3/1999 | Silver-Isenstadt et al. |
| 6,000,083 A | 12/1999 | Blaustein et al. |
| 6,178,579 B1 | 1/2001 | Blaustein et al. |
| 6,360,395 B2 | 3/2002 | Blaustein et al. |
| 7,600,285 B2 | 10/2009 | Jimenez et al. |
| 7,917,986 B2 | 4/2011 | Jimenez et al. |
| 7,941,924 B2 | 5/2011 | Jimenez et al. |
| 7,992,710 B2 | 8/2011 | Jimenez et al. |
| 8,161,591 B2 | 4/2012 | Gatzemeyer et al. |
| 2001/0002605 A1 | 6/2001 | Morawski et al. |
| 2001/0032796 A1 | 10/2001 | Rubenstein |
| 2003/0024841 A1* | 2/2003 | Murphy ............ B65D 5/00 206/459.5 |
| 2003/0028987 A1 | 2/2003 | Morawski et al. |
| 2003/0166373 A1 | 9/2003 | Whitney et al. |
| 2003/0213075 A1 | 11/2003 | Hui et al. |
| 2004/0078910 A1* | 4/2004 | Grote ............ A46B 15/0081 15/167.1 |
| 2005/0044646 A1 | 3/2005 | Peretz et al. |
| 2005/0220530 A1 | 10/2005 | Carmona |
| 2009/0050500 A1 | 2/2009 | Ultimo |
| 2009/0072610 A1 | 3/2009 | Sorrentino et al. |
| 2009/0313801 A1 | 12/2009 | Jimenez et al. |
| 2011/0125677 A1 | 5/2011 | Edelstein et al. |

FOREIGN PATENT DOCUMENTS

| | | |
|---|---|---|
| JP | 3100116 | 4/2004 |
| WO | WO 97/24079 | 7/1997 |
| WO | WO 03/075786 | 9/2003 |
| WO | WO 2009/148440 | 12/2009 |

OTHER PUBLICATIONS

International Search Report and the Written Opinion of the International Searching Authority issued in International Application PCT/US2011/060294 mailed Mar. 29, 2012.

Written Opinion of the International Preliminary Examining Authority issued in International Application PCT/US2011/060294 mailed Dec. 4, 2012.

\* cited by examiner

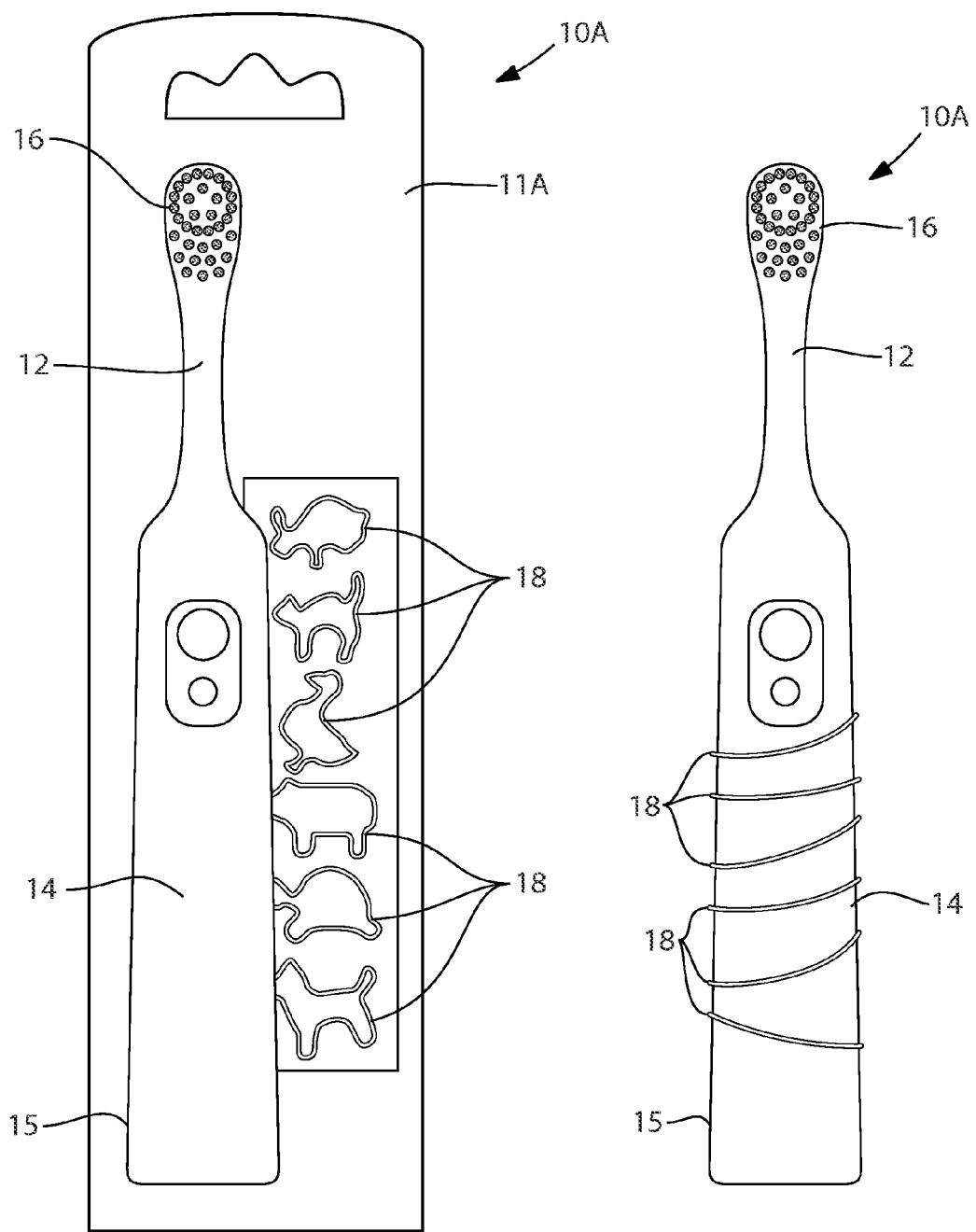

TOOTHBRUSH INCLUDING KIT FOR DECORATING THE TOOTHBRUSH

CROSS-REFERENCE TO RELATED APPLICATIONS

This application is a continuation of U.S. patent application Ser. No. 13/992,167, filed Jun. 6, 2013, now allowed, which is a U.S. national stage application under 35 U.S.C. §371 of International Application No. PCT/US2011/060294, filed Nov. 11, 2011, which in turn is a continuation-in-part of International Application No. PCT/US2011/031670, filed Apr. 8, 2011, and claims the benefit of U.S. Provisional Application No. 61/424,730, filed Dec. 20, 2010. The disclosures of the above applications are incorporated herein by reference.

BACKGROUND

Children's toothbrush handles are often fancifully decorated with colorful stickers having generic or licensed designs. Such designs may not only be attractive and aesthetically pleasing, but typically drive the purchase decision amongst a variety of toothbrushes adorned with different designs.

It would be desirable to provide a toothbrush handle to be decorated by a user, such as a child.

BRIEF SUMMARY

In one aspect of the present invention, a kit for decorating a toothbrush includes a toothbrush which has a base portion having an outer perimeter and a brush portion. The kit further includes at least one decorative band sized to fit around the outer perimeter of the base portion of the toothbrush. The kit may further include at least one sticker sized to fit on the base portion of the toothbrush.

In another aspect, the invention may be a toothbrush kit comprising: a package; a toothbrush having a base portion and a brush portion; and a sticker panel comprising three panel sections and a plurality of stickers positioned on at least one of the three panel sections; and wherein the toothbrush and the sticker panel are disposed within the package.

In yet another aspect, the invention may be a toothbrush kit comprising: a package; a powered toothbrush having a base portion having an outer perimeter and a brush portion; a plurality of decorative bands sized to fit around the outer perimeter of the base portion of the toothbrush, each of the decorative bands being made of an elastic material so that it can stretch to fit around the outer perimeter of the toothbrush; and wherein the powered toothbrush and the plurality of decorative bands are disposed within the package.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 schematically illustrates a toothbrush kit with a toothbrush and elements for decorating the toothbrush in accordance with a first embodiment of the present invention.

FIG. 2 schematically illustrates the toothbrush of FIG. 1 with the decorative elements attached thereto in accordance with a first embodiment of the present invention.

DETAILED DESCRIPTION

Figure 3:
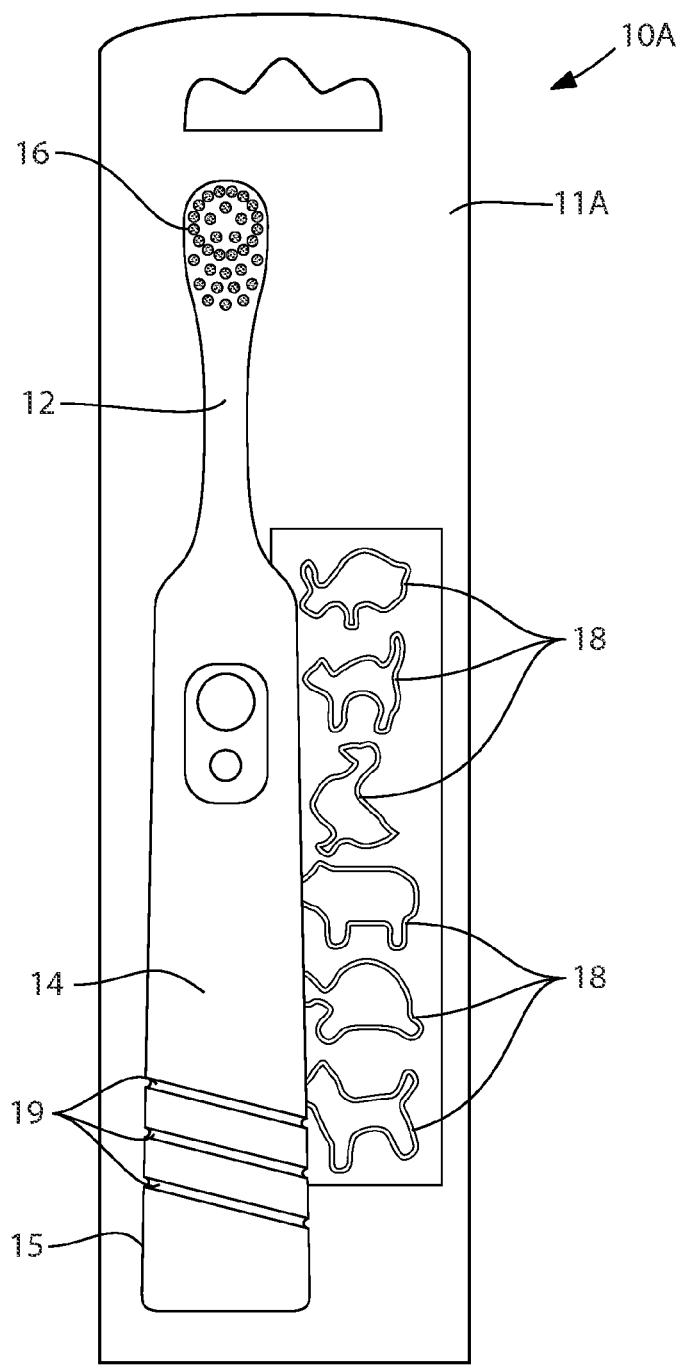
FIG. 3 schematically illustrates a toothbrush kit with a toothbrush and elements for decorating the toothbrush in accordance with a first embodiment of the present invention.

The following description of the preferred embodiment(s) is merely exemplary in nature and is in no way intended to limit the invention, its application, or uses.

The following detailed description is not intended to be understood in a limiting sense, but to be an example of the invention presented solely for illustration thereof, and by reference to which in connection with the following description and the accompanying drawings one skilled in the art may be advised of the advantages and construction of the invention. In the various views of the drawings, like reference characters designate like or similar parts.

Referring now to the drawings, there is shown in FIGS. 1-8 various toothbrushes including various kits for decorating the toothbrushes in accordance with several preferred embodiments of the present invention.

As can be seen in FIGS. 1 and 2, a first preferred embodiment of a toothbrush kit 10A is provided. FIG. 1 shows the toothbrush kit 10A in kit form (that is, in a package 11A that would appear in a retail store), prior to assembly of the elements of the kit 10A. FIG. 2 shows the toothbrush kit 10A subsequent to use of the various elements of the kit 10A. The kit 10A includes a toothbrush 12 having a base portion 14 having an outer perimeter 15 and a brush portion 16. At least one decorative band 18 is included in the kit 10A, preferably many different bands of many different colors. The decorative bands 18 provided are sized to fit around the outer perimeter 15 of the base portion 14 of the toothbrush 12. The bands 18 may be made of an elastic material so that they can stretch to fit the outer perimeter 15 of the toothbrush 12. When the bands 18 are removed from the perimeter 15, they will return to their original shape and size. The bands 18 in an unstretched mode can have a variety of shapes. The outer perimeter 15 of the toothbrush may include grooves 19 into which the outer surface of the bands 18 can be inserted (see FIGS. 3 and 4). The kit 10A of the first embodiment may further include at least one sticker 20 sized to fit on the base portion 14 of the toothbrush 12. See FIG. 9, described below.

Figure 4:
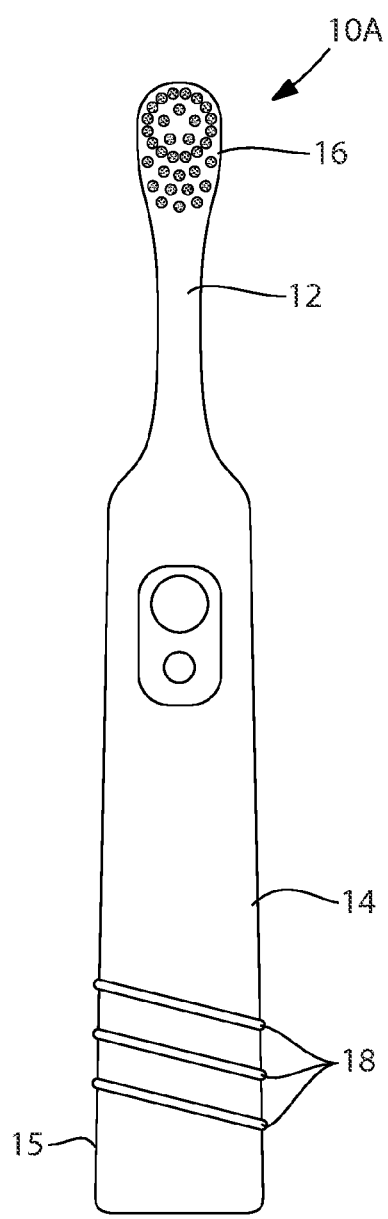
FIG. 4 schematically illustrates the toothbrush of FIG. 1 with the decorative elements attached thereto in accordance with a first embodiment of the present invention.

As can be seen in FIGS. 3 and 4, a variation of the toothbrush kit 10A is provided. FIG. 3 shows the toothbrush kit 10A in kit form (that is, in a package 11A that would appear in a retail store), prior to assembly of the elements of the kit 10A. FIG. 4 shows the toothbrush kit 10A subsequent to use of the various elements of the kit 10A. The kit 10A includes a toothbrush 12 having a base portion 14 having an outer perimeter 15 and a brush portion 16. At least one decorative band 18 is included in the kit 10A, preferably many different bands of many different colors. The decorative bands 18 provided are sized to fit around the outer perimeter 15 of the base portion 14 of the toothbrush 12. The bands 18 may be made of an elastic material so that they can stretch to fit the outer perimeter 15 of the toothbrush 12. When the bands 18 are removed from the perimeter 15, they will return to their original shape and size. The bands 18 in an unstretched mode can have a variety of shapes. In the embodiment as shown, the bands 18 are in the shape of animals. In other embodiments, the bands 18 could be in the shape of any polygon, such as a rectangle or a pentagon.

The outer perimeter 15 may include one or more groove 19. The groove 19 may be formed in such a manner so as to receive the outer surface of the bands 18. In the embodiment as shown, the outer perimeter 15 includes three grooves 19. It is understood that more or less groove 19 may be formed on the outer perimeter 15. The groove 19 may be provided to assist in retaining the band 18 so that the band 18 does not slide along the base portion 14. The groove 19 may also provide additional aesthetic appeal, such as introducing a different texture on base portion 14. The groove 19 may further provided as an indication to a user as to a location for holding the toothbrush 12.

Figure 5:
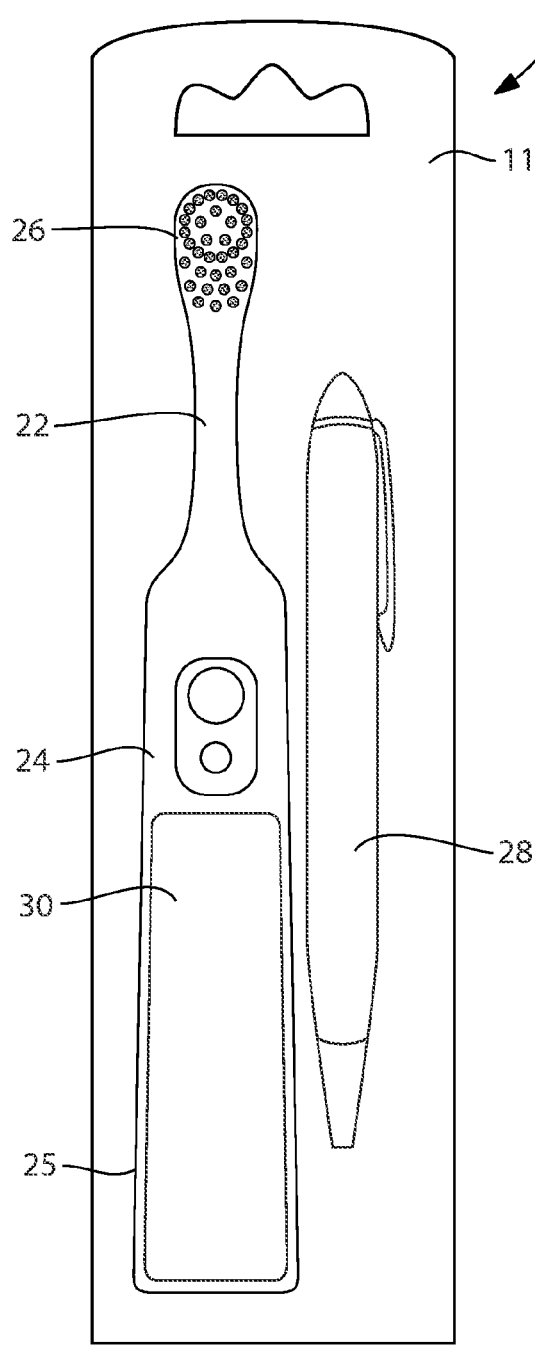
FIG. 5 schematically illustrates a toothbrush kit with a toothbrush and an element for decorating the toothbrush according to a second embodiment of the present invention.
Figure 6:
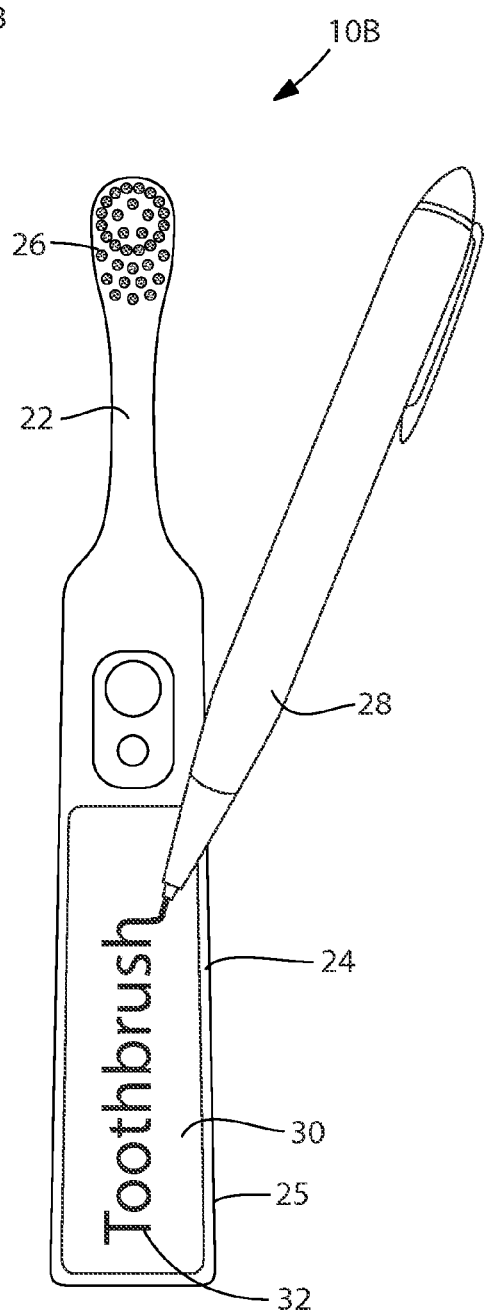
FIG. 6 schematically illustrates the toothbrush and the element for decorating the toothbrush of FIG. 5 in use according to a second embodiment of the present invention.

As can be seen in FIGS. 5 and 6, a second preferred embodiment of a toothbrush kit 10B is provided. FIG. 5 shows the toothbrush kit 10B in kit form (that is, in a package 11B that would appear in a retail store), prior to use of the elements of the kit 10B. FIG. 4 shows the toothbrush kit 10B subsequent to use of the various elements of the kit 10B. The kit 10B includes a toothbrush 22 having a base portion 24 having an outer perimeter 25 and a brush portion 26. At least one writing instrument 28 is included in the kit 10B, preferably several different writing instruments 28 in different colors. The toothbrush 22 has an area designated thereon for marking 30 with the writing instruments 28. In particular, the writing instruments 28 provided may be used by, for example, a child to draw pictures and/or write his or her name on the area designated for marking 30 on the toothbrush 22. The area designated for marking 30 on the toothbrush 22 must have a finish that is capable of receiving ink 32 or other material used for writing by the writing instrument 28. Preferably, the area designated for marking can be easily wiped clean of the ink so that the user can erase and reuse the area 28 for various markings. Furthermore, the ink of the marker should be washable ink. Again, the kit 10B may further include at least one sticker 20 sized to fit on the base portion 14 of the toothbrush 12. See FIG. 9 described below. While not shown, one or more grooves 19 may also be included on a portion of the base portion 14 of the toothbrush 12 in kit 10B.

Figures 7, 8:
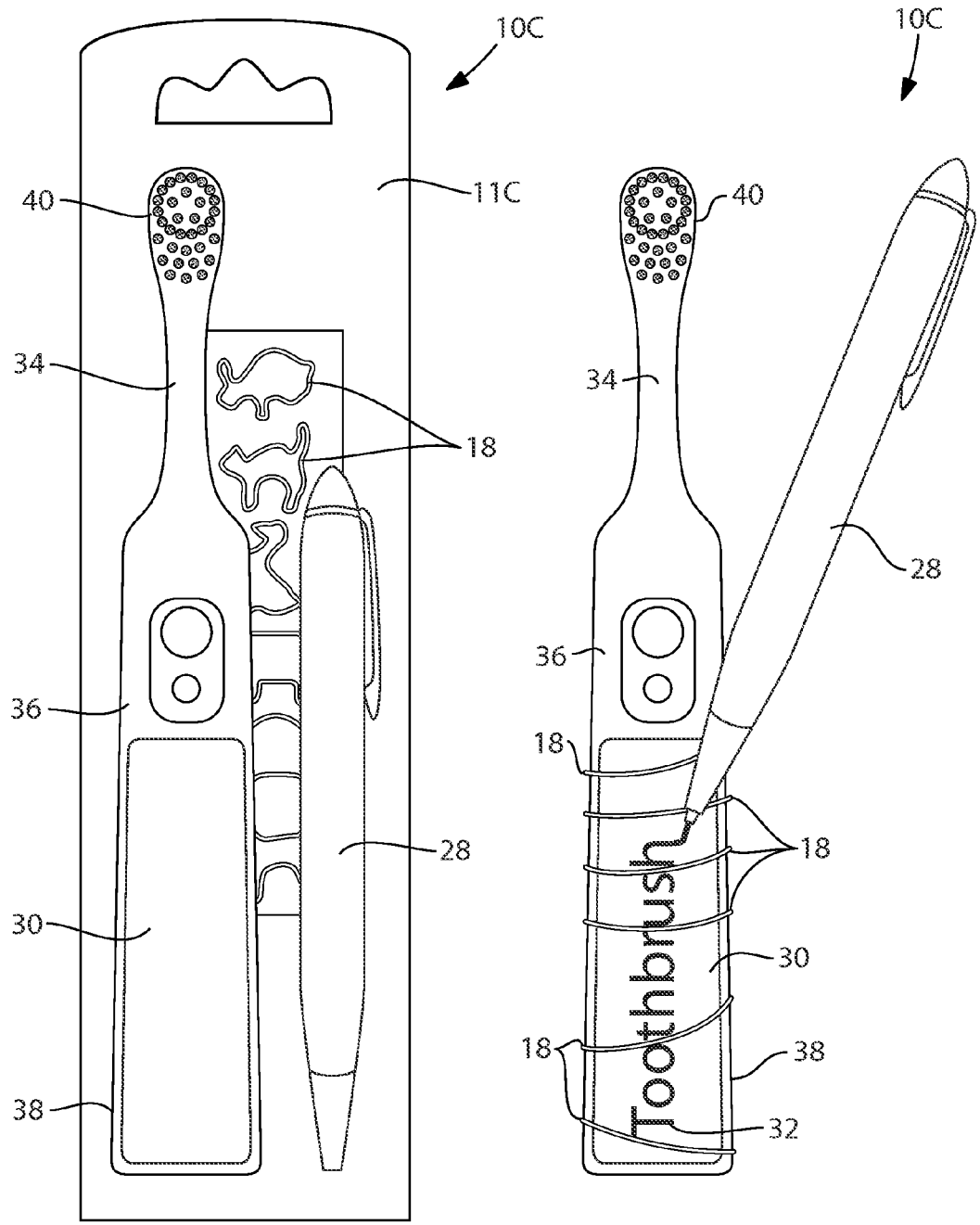
FIG. 7 schematically illustrates a toothbrush kit with a toothbrush and elements for decorating the toothbrush in accordance with a third embodiment of the present invention.
FIG. 8 schematically illustrates the toothbrush and the element for decorating the toothbrush of FIG. 7 in use according to a third embodiment of the present invention.

As can be seen in FIGS. 7 and 8, a third preferred embodiment of a toothbrush kit 10C is provided. FIG. 7 shows the toothbrush kit 10C in kit form (that is, in a package 11C that would appear in a retail store), prior to use of the elements of the kit 10C. FIG. 8 shows the toothbrush kit 10C subsequent to use of the various elements of the kit 10C. The kit 10C includes a toothbrush 34 having a base portion 36 having an outer perimeter 38 and a brush portion 40. At least one writing instrument 28 is included in the kit 10C, preferably several different writing instruments 28 in different colors. The toothbrush 34 has an area designated thereon for marking 30 with the writing instruments 28. In particular, the writing instruments 28 provided may be used by, for example, a child to draw pictures and/or write his or her name on the area designated for marking 30 on the toothbrush 34. The area designated for marking 30 on the toothbrush 34 must have a finish that is capable of receiving ink 32 or other material used for writing by the writing instrument 28. Additionally, the kit 10C includes at least one decorative band 18, preferably many different bands of many different colors. The decorative bands 18 provided are sized to fit around the outer perimeter 38 of the base portion 36 of the toothbrush 34. Again, the kit 10C may further include at least one sticker 20 sized to fit on the base portion 36 of the toothbrush 34. While not shown, one or more grooves 19 may also be included on a portion of the base portion 14 of the toothbrush 12 in kit 10C.

Figure 9:
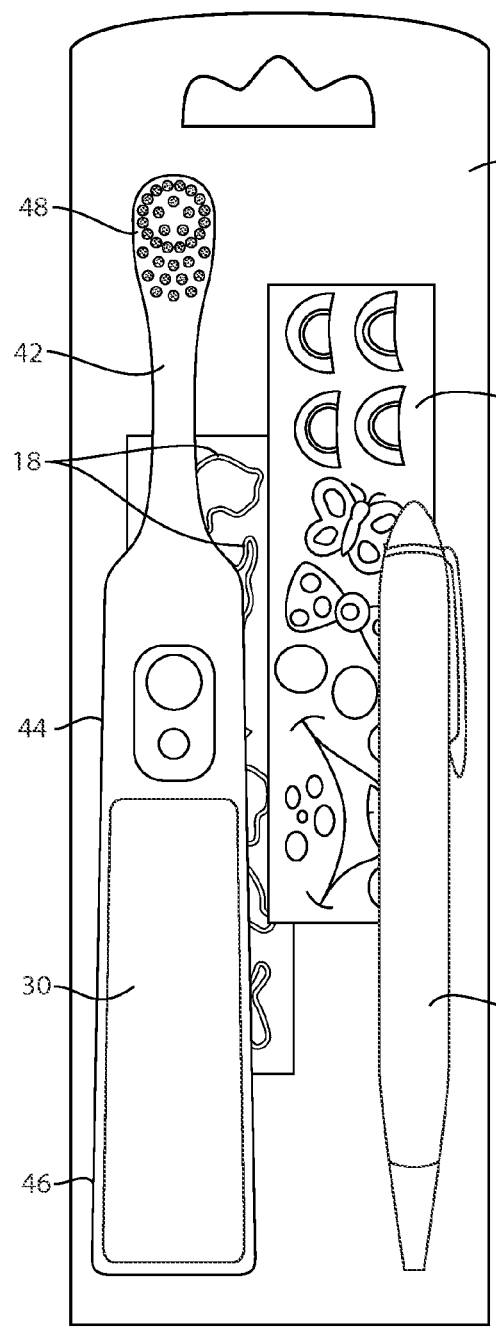
FIG. 9 schematically illustrates a toothbrush kit with a toothbrush and elements for decorating the toothbrush according to a fourth embodiment of the present invention.
Figure 10:
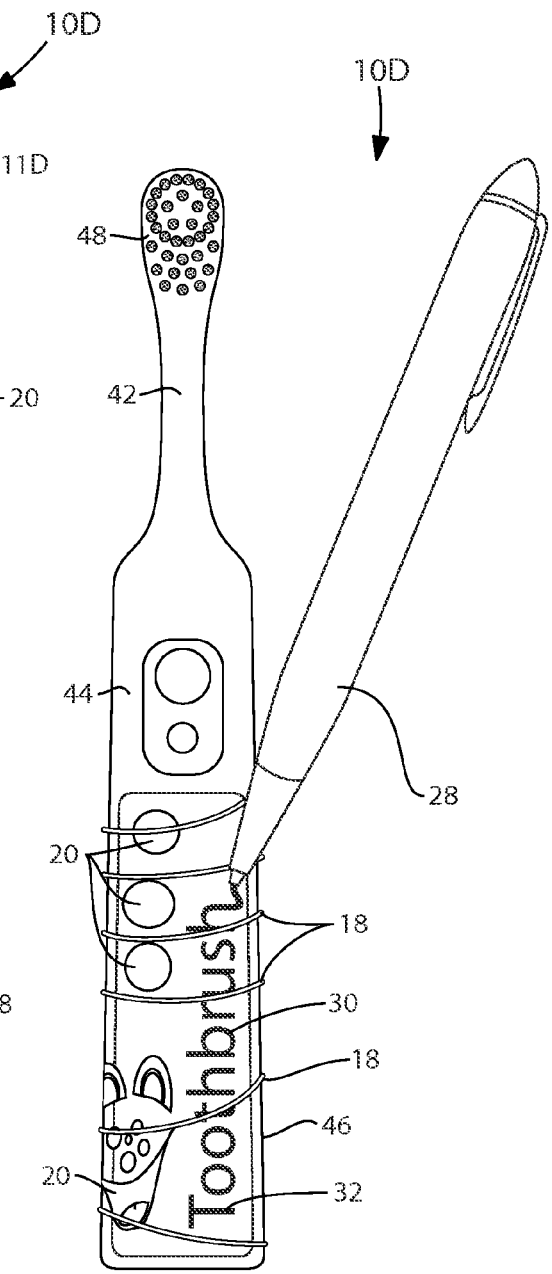
FIG. 10 schematically illustrates the toothbrush and the element for decorating the toothbrush of FIG. 9 in use according to a fourth embodiment of the present invention.

Finally, as can be seen in FIGS. 9 and 10, a fourth preferred embodiment of a toothbrush kit 10D is provided. FIG. 9 shows the toothbrush kit 10D in kit form (that is, in a package 11D that would appear in a retail store), prior to use of the elements of the kit 10D. FIG. 10 shows the toothbrush kit 10D subsequent to use of the various elements of the kit 10D. The kit 10D includes a toothbrush 42 having a base portion 44 having an outer perimeter 46 and a brush portion 48. At least one writing instrument 28 is included in the kit 10D, preferably several different writing instruments 28 in different colors. The toothbrush 42 has an area designated thereon for marking 30 with the writing instruments 28. In particular, the writing instruments 28 provided may be used by, for example, a child to draw pictures and/or write his or her name on the area designated for marking 30 on the toothbrush 42. The area designated for marking 30 on the toothbrush 42 must have a finish that is capable of receiving ink 32 or other material used for writing by the writing instrument 28. Additionally, the kit 10D includes at least one decorative band 18, preferably many different bands of many different colors. The decorative bands 18 provided are sized to fit around the outer perimeter 46 of the base portion 44 of the toothbrush 42. Again, the kit 10D may further include at least one sticker 20 sized to fit on the base portion 48 of the toothbrush 46. While not shown, one or more grooves 19 may also be included on a portion of the base portion 14 of the toothbrush 12 in kit 10D.

While not shown, any of kit 10A-10D may include a display window comprised of a transparent thermoformed polymeric material such that the toothbrush 12, the decorative bands 18, and/or the sticker 20 may be entirely or at least partially visible through the display window and substantially impervious to outside elements. The display window may be comprised of a polymeric material such as polyvinyl chloride (PVC) or polyethylene terephthalate (PET). However, the display window may be comprised of any polymeric material known for use in blister pack or clam-shell type packaging and may alternatively be comprised of any material or combination of materials, including partially transparent, semi-transparent, and/or opaque materials and may be formed in any manner such as injection or blow molding. The display window helps to make a portion of the toothbrush 12, the decorative bands 18, and/or the sticker 20 visible to a consumer, so that the consumer has an opportunity to select a kit 10A-10D that may be appealing to him or her.

Figure 11:
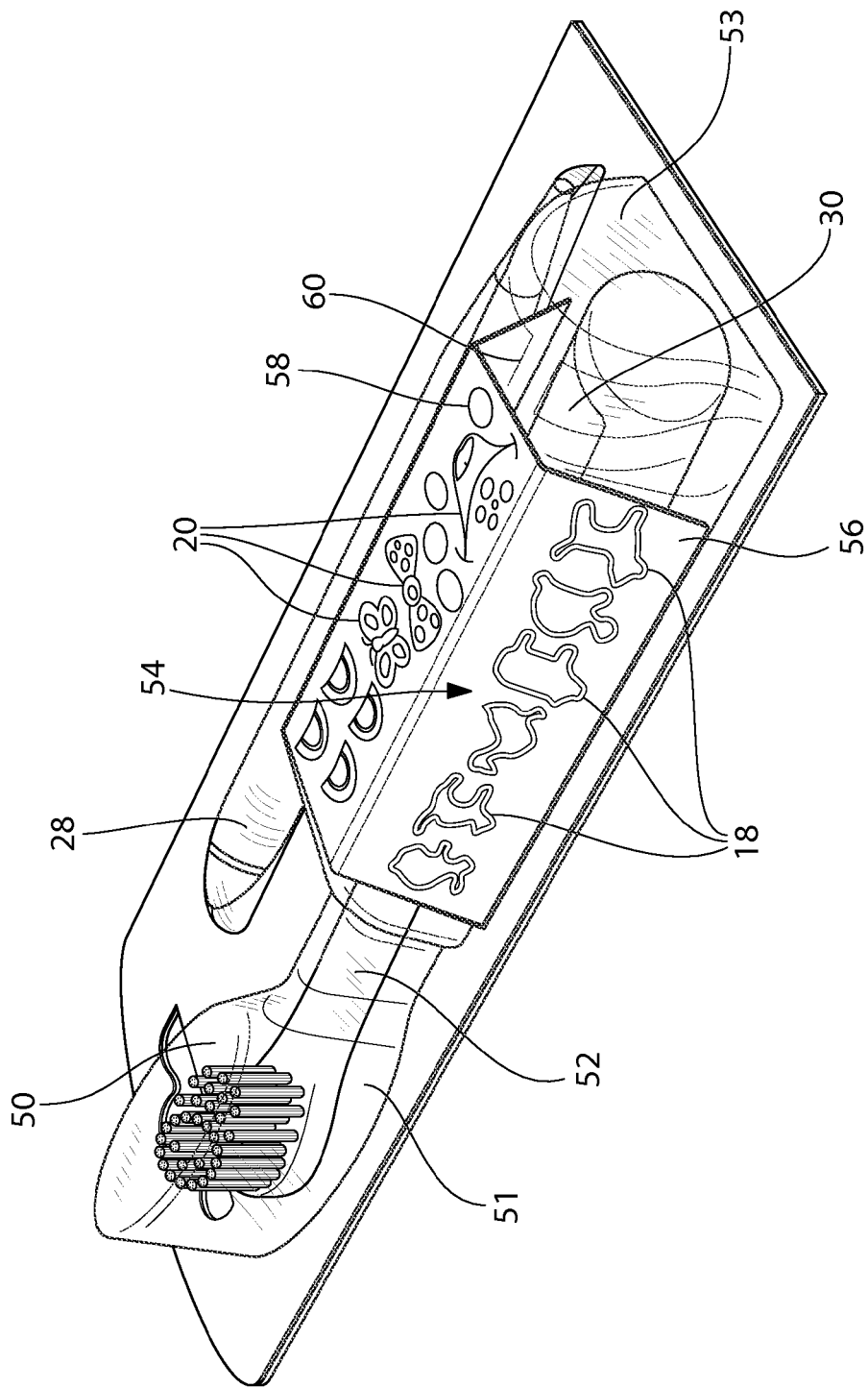
FIG. 11 schematically illustrates a toothbrush kit with a toothbrush and elements for decorating the toothbrush in accordance with a fifth embodiment of the present invention

Referring to FIG. 11, in some embodiments, any of kit 10A-10D may include a package 50, a toothbrush 52, a panel 54, and the writing instrument 28. In some embodiments, the package 50 may be a blister pack or a clam-shell type packaging. The package 50 may include a three-dimensional front cover 51. In some embodiments, the front cover 51 may be substantially transparent, semi-transparent, opaque, and/or a combination thereof. As shown in FIG. 11, the front cover 51 is contoured to form a receiving cavity 53. In the exemplified embodiment, the entirety of the toothbrush 52 and the panel 54 are disposed within the receiving cavity 53, while the writing instrument 28 is disposed within the package 50 in a separate receiving cavity. In alternate embodiments, the toothbrush 52, the panel 54, and the writing instrument 28 may be disposed within a single receiving cavity. In some embodiments, the panel 54 includes three panel sections 56, 58, and 60, and forms a sleeve through which a portion of the toothbrush 52 extends. The panel 54 may include one or more decorative bands 18 and one or more stickers 20. Of course, in other embodiments, the panel 54 may include the decorative bands 18 only or the panel 54 may include stickers 20 only. In the embodiment as shown, a front surface of each of the panel sections 56, 58, and 60 is visible through the front cover 51 such that the decorative bands 18 and/or the stickers 20 are visible through the front cover 51.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

What is claimed is:
1. A toothbrush kit comprising:
   a package comprising:
      a toothbrush having a base portion and a brush portion; and
      a sticker panel comprising three panel sections and a plurality of stickers positioned on at least one of the three panel sections for decorating the base portion of the toothbrush;
   wherein the sticker panel forms a sleeve through which a portion of the toothbrush extends, at least one of the plurality of stickers visible from outside of the package through a substantially transparent portion of the package, at least a portion of the toothbrush protruding from the sleeve formed by the sticker panel and being visible from outside of the package.
2. The toothbrush kit of claim 1 wherein at least one of the plurality of stickers is positioned on each of the three panel sections.
3. The toothbrush kit of claim 1 wherein the package comprises a single receiving cavity, and wherein the toothbrush and the sticker panel are disposed within the single receiving cavity.
4. The toothbrush kit of claim 1 wherein the toothbrush is a powered toothbrush.
5. The toothbrush kit of claim 1 wherein the three panel sections comprise a first panel section, a second panel section, and a third panel section, and wherein the first and second panel sections are coupled at a first fold line and the second and third panel sections are coupled at a second fold line.
6. The toothbrush kit of claim 5 wherein the first and second panel sections can fold relative to one another about the first fold line and wherein the second and third panel sections can fold relative to one another about the second fold line.
7. The toothbrush kit of claim 1 wherein the package comprises a blister package, and wherein the substantially transparent portion of the package is a three-dimensional front cover of the package that forms a receiving cavity for retaining the toothbrush and the sticker panel.
8. The toothbrush kit of claim 1 wherein each of the plurality of stickers is sized to fit on the base portion of the toothbrush for decoration of the toothbrush by a user.
9. The toothbrush kit of claim 1 further comprising a plurality of decorative bands, each of the decorative bands being made of an elastic material so that it can stretch to fit around an outer perimeter of the toothbrush, and wherein the toothbrush, the plurality of stickers, and the plurality of decorative bands are disposed within a single receiving cavity of the package.
10. A toothbrush kit comprising:
    a package comprising;
       a toothbrush having a base portion having an outer perimeter and a brush portion; and
       a plurality of decorative bands, each of the decorative bands being made of an elastic material so that it can stretch to fit around the outer perimeter of the base portion of the toothbrush;
    wherein the plurality of decorative bands are positioned on a panel within the package, the panel forming a sleeve through which a portion of the toothbrush extends, at least one of the decorative bands visible from outside of the package through a substantially transparent portion of the package, and wherein at least a portion of the toothbrush protrudes from the sleeve and is visible from outside of the package.
11. The toothbrush kit of claim 10 wherein each of the decorative bands is in the shape of an animal when in an unstretched state.
12. The toothbrush kit of claim 10 wherein each of the decorative bands is a different color.
13. The toothbrush kit of claim 10 wherein the panel comprises three panel sections, and wherein at least one of the plurality of decorative bands is positioned on each of the three panel sections.
14. The toothbrush kit of claim 10 wherein the package comprises a single receiving cavity, and wherein the toothbrush is powered and the plurality of decorative bands are disposed within the single receiving cavity.
15. A toothbrush kit comprising:
    a package comprising;
       a toothbrush having a base portion having an outer perimeter and a brush portion, a plurality of grooves formed into the outer perimeter of the base portion of the toothbrush; and
       a plurality of decorative bands, each of the decorative bands being made of an elastic material so that it can stretch to fit around the outer perimeter of the base portion of the toothbrush; and
    wherein each of the grooves is configured to receive one of the decorative bands.
16. The toothbrush kit of claim 15 wherein the plurality of grooves are formed into the outer perimeter of the base portion of the toothbrush in a spaced apart manner.
17. The toothbrush kit of claim 16 wherein each of the plurality of grooves retains one of the decorative bands therein so that the decorative band does not slide along the base portion of the toothbrush.

* * * * *